United States Patent
Iinaga

(10) Patent No.: US 11,000,214 B2
(45) Date of Patent: May 11, 2021

(54) PHYSICAL CONDITION MANAGEMENT DEVICE AND METHOD FOR SAME

(71) Applicant: MEDICAL PHOTONICS CO., LTD., Hokkaido (JP)

(72) Inventor: Kazuya Iinaga, Hokkaido (JP)

(73) Assignee: MEDICAL PHOTONICS CO., LTD., Hokkaido (JP)

( * ) Notice: Subject to any disclaimer, the term of this patent is extended or adjusted under 35 U.S.C. 154(b) by 480 days.

(21) Appl. No.: 16/075,435

(22) PCT Filed: Feb. 14, 2017

(86) PCT No.: PCT/JP2017/005261
§ 371 (c)(1),
(2) Date: Aug. 3, 2018

(87) PCT Pub. No.: WO2017/141895
PCT Pub. Date: Aug. 24, 2017

(65) Prior Publication Data
US 2019/0046091 A1    Feb. 14, 2019

(30) Foreign Application Priority Data

Feb. 18, 2016    (JP) .............................. JP2016-028553

(51) Int. Cl.
*A61B 5/1455*    (2006.01)
*G01N 21/17*    (2006.01)
(Continued)

(52) U.S. Cl.
CPC ........ *A61B 5/1455* (2013.01); *A61B 5/14546* (2013.01); *A61B 5/4866* (2013.01);
(Continued)

(58) Field of Classification Search
CPC ..... A61B 5/1455; A61B 5/14546; A61B 5/72; A61B 5/7271; A61B 5/0059–0091; G01N 21/47
See application file for complete search history.

(56) References Cited

U.S. PATENT DOCUMENTS 7,167,734 B2 *    1/2007  Khalil ................ A61B 5/14532
                                                     600/310
10,863,934 B2 *  12/2020  Iinaga .................. A61B 5/1455
(Continued)

FOREIGN PATENT DOCUMENTS

JP    2002-139501    5/2002
JP    2004-138454    5/2004
(Continued)

OTHER PUBLICATIONS

International Search Report dated Apr. 11, 2017 in International (PCT) Application No. PCT/JP2017/005261.
(Continued)

*Primary Examiner* — Meredith Weare
(74) *Attorney, Agent, or Firm* — Wenderoth, Lind & Ponack, L.L.P.

(57) ABSTRACT

A physical condition management device and a method thereof capable of performing early detection of metabolic disease, nutritional guidance, and a physical condition management diagnosis. The physical condition management device includes: an irradiation unit configured to radiate light at a predetermined light intensity toward an inside of a living body from outside of the living body; a light intensity detection unit configured to detect light intensity emitted from the living body; a scattering coefficient calculation unit configured to calculate a scattering coefficient of light inside the living body on the basis of the detected light intensity; a particle diameter calculation unit configured to calculate a variation of an average particle diameter of a lipid in blood
(Continued)

on the basis of a variation of the scattering coefficient; and a physical condition determination unit configured to determine a physical condition from a temporal change in the variation of the average particle diameter.

20 Claims, 11 Drawing Sheets

(51) Int. Cl.
    *A61B 5/145*     (2006.01)
    *A61B 5/00*     (2006.01)
    *G01N 21/47*     (2006.01)

(52) U.S. Cl.
    CPC ........... *A61B 5/7278* (2013.01); *G01N 21/17* (2013.01); *G01N 21/47* (2013.01); *A61B 2562/0238* (2013.01)

(56) References Cited

U.S. PATENT DOCUMENTS

2003/0023151 A1* 1/2003 Khalil ................ A61B 5/14532
    600/309
2015/0313516 A1 11/2015 Shimizu et al.
2019/0192056 A1* 6/2019 Iinaga ................ A61B 5/1455

FOREIGN PATENT DOCUMENTS

| | | |
|---|---|---|
| JP | 2007-117221 | 5/2007 |
| JP | 2007-304012 | 11/2007 |
| JP | 2010-48703 | 3/2010 |
| WO | 2014/087825 | 6/2014 |

OTHER PUBLICATIONS

Extended European Search Report dated Jul. 25, 2019 in corresponding European Patent Application No. 17753152.2.
Kazuya Iinaga et al: "Attempt for Noninvasive Evaluation of in Vivo Triglyceride in Blood", 2014 36th Annual International Conference of the IEEE Engineering in Medicine and Biology Society, vol. 2013, Jul. 1, 2013 (Jul. 1, 2013), pp. 1214-1217, XP055605275, United States ISSN: 1094-687X, DOI: 10.1109/EMBC.2013.6609725 *the whole document*.

* cited by examiner

PHYSICAL CONDITION MANAGEMENT DEVICE AND METHOD FOR SAME

TECHNICAL FIELD

The present invention relates to a physical condition management device and a method for the same.

BACKGROUND ART

In recent years, with the rise in a national medical care expenditure, controlling the medical care expenditure is a great concern to the government or the public. A treatment cost of a disease caused by a life style disease accounts for one-third of the medical care expenditure. Under such a circumstance, there is a need to control the national medical care expenditure, extend a healthy life expectancy, and improve a quality of life (QOL). For achieving these goals, a specific medical examination has been implemented and people become more aware of a presymptomatic disease.

In particular, it is known that a metabolic syndrome, a screening candidate of the specific medical examination, develops diabetes, dyslipidemia, and hypertension caused by insulin resistance due to accumulation of visceral fat obesity. It is expected that early detection of the metabolic syndrome leads to prevention of disease progression, improvement of QOL, and control of the national medical care expenditure.

As described above, the insulin resistance is an important factor for early detection of the life style disease, however, measuring abdominal girth is the only available method for predicting a risk of the insulin resistance in the specific medical examination.

Recently, it has been found that the insulin resistance is closely related to postprandial hyperlipidemia. It is also suggested that the postprandial hyperlipidemia may cause the insulin resistance. The postprandial hyperlipidemia is thought to be a metabolism disorder causing the metabolic syndrome. Thus, the postprandial hyperlipidemia is drawing attention not only as an indicator of an initial stage (a presymptomatic disease) of the metabolic syndrome, but also as a risk factor of arteriosclerosis. For example, it can be said that a risk of the onset of a coronary heart disease becomes higher as a non-fasting triglyceride concentration increases.

A lipid in the blood, due to its high hydrophobicity, forms a micelle covered with an amphiphilic phospholipid and exists in a particle form. Some lipid in the blood has a lipoprotein bound to its surface and is thus called the lipoprotein.

The lipoproteins are roughly classified into four types in accordance with a specific gravity. The lipoproteins are classified as chylomicron (CM), VLDL, LDL, and HDL in increasing order of the specific gravity. Further, the lipoproteins are classified as CM, VLDL, LDL, and HDL in decreasing order of a particle diameter.

The lipoprotein is an assembly of a cholesterol and a triglyceride (TG). A blood test measures the triglyceride and the cholesterol, each being a minimum unit of a constituent component of the lipoprotein.

For example, an LDL cholesterol usually called a bad cholesterol is measured as a cholesterol concentration included in an LDL particle. Measuring TG concentration in the LDL particle gives a LDL-TG value.

Further, there are originally four types of lipids. Of these, the LDL cholesterol and an HDL cholesterol are each known to be an indicator related to arteriosclerosis.

Further, a size reduction of the lipoprotein is considered a sign of the metabolic syndrome. A conventional technique includes a method of detecting the metabolic syndrome by measuring a concentration of a small dense LDL cholesterol in a test sample collected from an examinee (for example, see Patent Literature 1).

On the other hand, the large lipoproteins, CM and VLDL, are not actively measured in the clinical practice. Further, whether the size increase of the lipoprotein has any significance in a clinical or health evaluation has not been established.

Further, other measuring methods include an analysis method of a lipoprotein subclass, which includes a step of separating and extracting from a test sample a subclass of the lipoprotein on the basis of an individual phenotype of metabolic dynamics obtained by a waveform analysis of a lipoprotein profile and a step of determining a quantity of the lipoprotein subclass thus separated (for example, see Patent Literature 2).

CITATION LIST

Patent Literature

Patent Literature 1: JP2007-304012
Patent Literature 2: JP2002-139501

SUMMARY OF INVENTION

Technical Problem

However, the techniques in Patent Literature 1 and Patent Literature 2 are an examination method performed after blood collection, and they are not an examination methods performed in a time course manner.

Patent Literature 1 describes the method of detecting the metabolic syndrome by measuring the small dense LDL in the serum. According to Patent Literature 1, the LDL having a smaller diameter than the normal LDL, that is, the small dense LDL, is produced by disturbance of metabolism in the living body. In Patent Literature 1, the metabolic syndrome is detected by examining a concentration of the small dense LDL.

However, the method in Patent Literature 1 requires blood collection, serum separation, and the like. Since the method requires a physician's instruction and a special instrument for performing the above-described operations, the test cannot be easily performed at home or the like.

In Patent Literature 2, a particle diameter distribution of the lipoprotein contained in the serum is measured by a chromatogram such as an HPLC method to examine a CETP deficiency, the concentration of the small dense LDL, and the like. However, the method in Patent Literature 2 can only obtain single-time-point information at the time of blood collection and thus has the difficulty in accurately capturing information on the living body that is continuously changing on a daily basis.

Further, in a modern society where people eat three meals a day, people generally spend most of their waking time in the postprandial state. The metabolic disease progresses in accordance with a postprandial blood condition. Thus, collecting the blood only once during the fasting time is insufficient for screening the metabolic disease.

The present invention has been made to solve such conventional problems, and an object of the present invention is to provide a device and method capable of determining a physical condition.

Solution to Problem

A physical condition management device of the present invention includes: an irradiation unit configured to radiate light at a predetermined light intensity toward an inside of a living body from an outside of the living body; a light intensity detection unit configured to detect a light intensity emitted from the living body, the light intensity detection unit being arranged at a predetermined interval from a light irradiation position of the irradiation unit; a scattering coefficient calculation unit configured to calculate a scattering coefficient of light inside the living body on the basis of the light intensity detected by the light intensity detection unit; a particle diameter calculation unit configured to calculate a variation of an average particle diameter of a lipid in blood on the basis of a variation of the scattering coefficient; and a physical condition determination unit configured to determine a physical condition from a temporal change in the variation of the average particle diameter.

Further, an operation method of a physical condition management device of the present invention includes: an irradiation step of radiating light at a predetermined light intensity toward an inside of a living body from an outside of the living body; a light intensity detection step of detecting a light intensity emitted from the living body at a position of a predetermined interval from a light irradiation position in the irradiation step; a scattering coefficient calculation step of calculating a scattering coefficient of light inside the living body on the basis of the light intensity detected in the light intensity detection step; a particle diameter calculation step of calculating a variation of an average particle diameter of a lipid in blood on the basis of a variation of the scattering coefficient; and a physical condition determination step of determining a physical condition from a temporal change in the variation of the average particle diameter.

Further, a physical condition management device of the present invention is communicatively connected to a user device that includes an irradiation unit configured to radiate light at a predetermined light intensity toward an inside of a living body from an outside of the living body, a light intensity detection unit configured to detect a light intensity emitted from the living body for measuring an attenuation of the light intensity of the radiated light corresponding to a radiation-detection distance, the light intensity detection unit being arranged at a predetermined interval from or continuously with a light irradiation position of the irradiation unit, and a communication unit configured to send the light intensity detected by the light intensity detection unit, the physical condition management device including: a scattering coefficient calculation unit configured to calculate a scattering coefficient of the light inside the living body on the basis of the light intensity sent from the user device; a particle diameter calculation unit configured to calculate a variation of an average particle diameter of a lipid in the blood on the basis of a variation of the scattering coefficient; and a physical condition determination unit configured to determine a physical condition from a temporal change in the variation of the average particle diameter.

Advantageous Effects of Invention

According to the physical condition management device and the method thereof of the present invention, the early detection of the metabolic disease, a nutritional guidance, and a physical condition management diagnosis can be performed by measuring the variation of the average particle diameter of the lipid.

DESCRIPTION OF EMBODIMENTS

Figure 1:
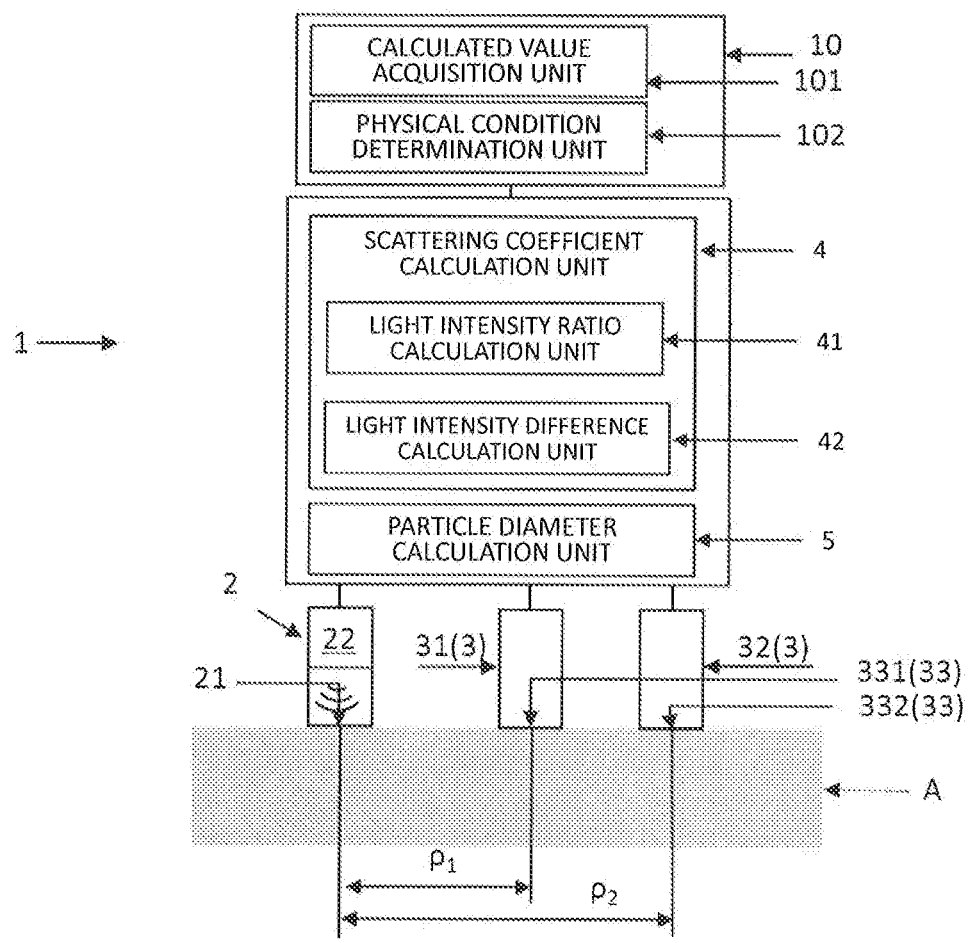
FIG. 1 is a diagram illustrating a configuration of a physical condition management device of the present embodiment.

Hereinafter, a physical condition management device and an operation method thereof, which are embodiments of the present invention, will be described in detail by referring to the drawings.

FIG. 1 is a diagram illustrating a configuration of a physical condition management device of the present embodiment. The physical condition management device of the present embodiment includes a CPU (arithmetic unit) and a memory device (storage unit such as a RAM and a ROM) and functions as a device shown in a block diagram in FIG. 1 by executing a program stored in the memory device.

As shown in FIG. 1, a physical condition management device 1 of the present embodiment includes: an irradiation unit 2 configured to radiate light toward an inside of a living body (A in FIG. 1) from an outside of the living body; a light intensity detection unit 3 configured to detect the light intensity at a predetermined detection position 31 outside the living body; a scattering coefficient calculation unit 4 configured to calculate a scattering coefficient $\mu_s'$ of the light inside the living body on the basis of the light intensity detected by the light intensity detection unit 3; a particle diameter calculation unit 5 configured to calculate a variation of an average particle diameter of a lipid such as a lipoprotein in the blood on the basis of the scattering coefficient $\mu_s'$ of the light calculated by the scattering coefficient calculation unit 4, and a physical condition management measuring device 10 that includes a physical condition determination unit 102 configured to determine a physical condition on the basis of a temporal change in the variation of the average particle diameter of the lipid.

As shown in FIG. 1, the irradiation unit 2 includes a light source 22 configured to radiate light toward the inside of the living body from the outside of the living body at a predetermined irradiation position 21. The light source 22 of the present embodiment can adjust a wavelength of the light to be radiated. The light source 22 can adjust the wavelength in a range other than the wavelength range in which the light is absorbed by inorganic matters in the blood plasma. The light source 22 can adjust the wavelength in a range other than the wavelength range in which light is absorbed by cellular components in the blood. The cellular components in the blood described herein include a red corpuscle, a white corpuscle, and a platelet in the blood. The inorganic matters in the blood plasma are water and an electrolyte in the blood.

Figure 2:
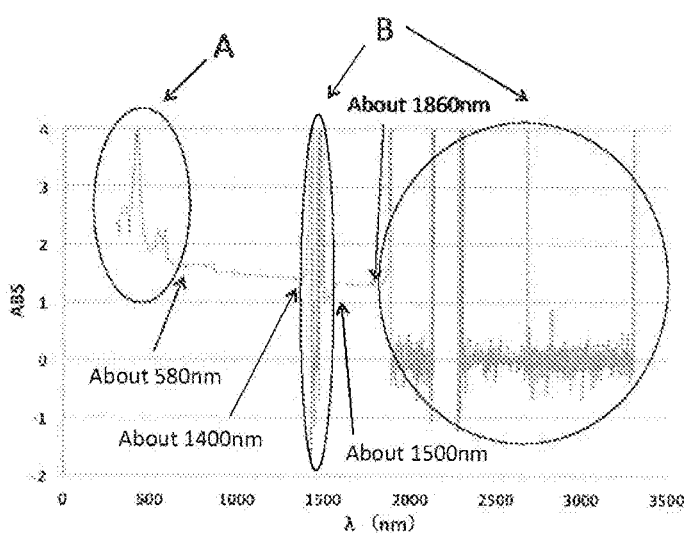
FIG. 2 is a diagram illustrating a light absorption spectrum of the blood.

FIG. 2 is a diagram illustrating an absorption spectrum of the blood. The wavelength range in which the light is absorbed by the inorganic matters in the blood plasma mainly refers to a range in which the light is strongly absorbed by the inorganic matters in the blood plasma as shown by B in FIG. 2. Similarly, the wavelength range in which the light is absorbed by the cellular components in the blood mainly refers to a range in which the light is strongly absorbed by the cellular components in the blood as shown by A in FIG. 2. In the wavelength range other than these ranges, light absorption by the inorganic matters in the blood plasma and light absorption by the cellular components in the blood are negligible in an experiment and a biological measurement.

As shown in FIG. 2, the wavelength range of the light source 22 is preferably set to about 1,400 nm or shorter, and about 1,500 nm to about 1,860 nm in consideration of the wavelength range in which the light is absorbed by the inorganic matters in the blood plasma. Further, the wavelength range of the light source 22 is preferably set to about 580 nm to about 1,400 nm and about 1,500 nm to about 1,860 nm in consideration of the wavelength range in which the light is absorbed by the cellular components in the blood.

Excluding the ranges indicated by A and/or B in FIG. 2 from the wavelength range used in the light source 22 prevents an influence of the light absorption by the inorganic matters in the blood plasma and an influence of the light absorption by the cellular components in the blood on the light detected by the light intensity detection unit 3 described below. This eliminates absorption high enough to identify a substance and reduces a light energy loss by absorption to a negligibly small level. Thus, the light in the blood is propagated far by the scattering caused by the lipid in the blood and emitted to the outside of the body.

Further, the irradiation unit 2 of the present embodiment can freely adjust a time length of light radiation, such as continuous light radiation and pulsed light radiation, in accordance with a calculation method of the scattering coefficient $\mu_s'$ performed by the scattering coefficient calculation unit 4 described below. The irradiation unit 2 can freely modulate the intensity and phase of the light to be radiated.

The irradiation unit 2 may adopt a light source 22 that uses a fixed wavelength. The irradiation unit 2 may adopt a plurality of light sources that use different wavelengths or radiate mixed light of a plurality of wavelengths.

The light intensity detection unit 3 receives the light emitted from the living body to the outside of the living body and detects the light intensity of the emitted light. In a case where a plurality of the light intensity detection units 3 are used, the light intensity detection units 3 are each arranged at a different distance from the irradiation position 21 serving as a substantial center. As shown in FIG. 1, in the present embodiment, a first light intensity detection unit 31 and a second light intensity detection unit 32 are arranged in this order in a straight line on the same plane at predetermined intervals from the irradiation position 21. The light intensity detection unit 3 may be a light receiving element such as a CCD and a CMOS.

As shown in FIG. 1, in the present embodiment, a distance from the irradiation position 21 to a first detection position 331 of the first light intensity detection unit 31 is defined as a first radiation-detection distance ρ1 and a distance from the irradiation position 21 to a second detection position 332 of the second light intensity detection unit 32 is defined as a second radiation-detection distance ρ2.

Figure 3:
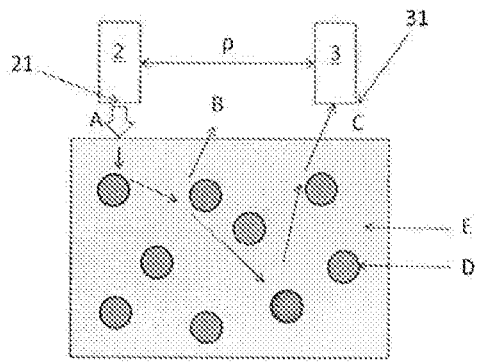
FIG. 3 is a diagram illustrating light scattering caused by a lipid in the blood.

As shown in FIG. 3, a predetermined distance p is provided between the irradiation position 21 from which the light is radiated to the living body and the detection position 31 at which the intensity of the light emitted from the blood (E in FIG. 3) in the living body is detected. Providing the predetermined distance p prevents an influence of the light (B in FIG. 3) directly emitted from the living body, which is caused by reflection of the radiated light (A in FIG. 3) by a scattering body on or near a surface of the living body. The radiated light reaches a depth where the lipid such as the lipoprotein is present and is then reflected by the lipid (D in FIG. 3) in the blood. The light reflected by the lipid is scattered and emitted from the living body as back scattered light (C in FIG. 3). The light intensity of the back scattered light is detected. Further, extending the distance p between the irradiation position 21 and the detection position 31 extends an optical path length. Thus, the light to be detected collides with the lipid more frequently and is greatly influenced by the scattering. Extending the distance ρ facilitates detection of the influence of the scattering that is hardly detected due to faintness.

The lipoprotein as a measurement object has a spherical structure covered with an apoprotein and the like. The lipoprotein behaves like a solid matter in the blood. The lipoprotein has light reflectivity. In particular, chylomicron (CM), VLDL, and the like, having a large particle diameter and specific gravity, contain a large amount of triglyceride (TG) and have characteristics of facilitating light scattering more easily. Thus, the light intensity detected by the light intensity detection unit 3 includes the influence of the light scattering caused by the lipoprotein.

Note that, in a case where a plurality of the detection positions 31 are arranged, a layout of the plurality of detection positions 31 is not limited to the linear form as long as they are arranged at different distances from the irradiation position 21 serving as the substantial center. The layout may be appropriately selected from a circular form, a wave form, a zigzag form, and the like. Further, the first radiation-detection distance ρ1 and the second radiation-detection distance ρ2 between the irradiation position 21 and the detection position 31, and an interval between the detection positions 331 and 332 are not limited to the predetermined intervals and they may be continuously arranged.

The scattering coefficient calculation unit 4 calculates the scattering coefficient $\mu_s'$ of the light inside the living body (including the blood, the skin, the muscle, etc.) on the basis of the light intensity detected by the light intensity detection unit 3. As described above, the light intensity detected by the light intensity detection unit 3 includes the influence of the light scattering caused by the lipoprotein. This feature is utilized to calculate the scattering coefficient $\mu_s'$. Note that the scattering coefficient $\mu_s'$ of the present embodiment is not limited to a value obtained by quantifying an efficiency of a general scattering process, but may include a value obtained by quantifying the influence of the scattering under a predetermined condition in consideration of a scattering phenomenon. A detailed description will be given below.

As shown in FIG. 1, the scattering coefficient calculation unit 4 of the present embodiment includes two calculation units, namely, a light intensity ratio calculation unit 42 and a light intensity difference calculation unit 43.

The light intensity ratio calculation unit 42 calculates the scattering coefficient $\mu_s'$ from a ratio of the light intensities detected by the plurality of light intensity detection units 3. The light intensity ratio calculation unit 42 calculates the scattering coefficient $\mu_s'$ on the basis of the scattering phenomenon in which the radiated light is more attenuated by the scattering as the distance to a detection position 33 is increased.

In the present embodiment, the continuous light having a predetermined light intensity is radiated from the irradiation unit 2, and the scattering coefficient $\mu_s'$ is calculated from a ratio of a first light intensity R(ρ1) detected by the first light intensity detection unit 31 and a second light intensity R(ρ2) detected by the second light intensity detection unit 32 (Equation 1).

$$\mu_s' = R(\rho 1)/R(\rho 2) \quad \text{(Equation 1)}$$

The light intensity difference calculation unit 43 calculates the scattering coefficient $\mu_s'$ from a difference of the light intensities detected by the plurality of light intensity detection units 3. As with the light intensity ratio calculation unit 42, the scattering coefficient $\mu_s'$ is calculated on the basis of the scattering phenomenon in which the radiated light is more attenuated by the scattering as the distance to the detection position 33 is increased.

The light intensity difference calculation unit 43 of the present embodiment calculates the scattering coefficient $\mu_s'$ from a difference of the light intensity R(ρ1) at the first detection position 331 and the light intensity R(ρ2) at the second detection position 332 (Equation 2).

$$\mu_s' = R(\rho 1) - R(\rho 2) \quad \text{(Equation 2)}$$

Note that the calculation method of the scattering coefficient $\mu_s'$ by the scattering coefficient calculation unit 4 is not limited to the above-described calculations.

The particle diameter calculation unit 5 calculates the variation of the average particle diameter of the lipoprotein in the blood on the basis of a variation of the scattering coefficient $\mu_s'$ calculated by the scattering coefficient calculation unit 4. In the present embodiment, statistical data on a relation between the variation of the scattering coefficient $\mu_s'$ and the variation of the average particle diameter of the lipoprotein are obtained, and then the actual variation of the average particle diameter of the lipoprotein is calculated by comparing the variation of the scattering coefficient $\mu_s'$ and the statistical data.

Note that no particular limitation is imposed on a format of the statistical data. The statistical data may be classified on the basis of, for example, gender, height, weight, and BMI, and the calculation may be performed by using a table, a graph, a function expression, and the like.

The average particle diameter of the lipoprotein described herein refers to a particle diameter expressed in a unit of "nm". The average particle diameter of the lipoprotein is generally as follows. CM: 80 to 1,000 nm, VLDL: 30 to 80 nm, LDL: 18 to 25 nm, HDL: 7.5 to 10 nm.

The average particle diameter described herein comprehensively includes the following variation and condition. Specifically, there are four types of the lipoproteins and variation in the number of particles also affects the scattering. Further, the number of the four types of the lipoprotein particles also slightly fluctuates. That is, the average particle diameter changes by the increase and decrease in the number of the large particle and the average particle diameter also changes by the increase and decrease in the number of the small particle. Thus, the average particle diameter changes when the large particle becomes larger (or smaller) and the average particle diameter also changes when the small particle becomes larger (or smaller).

As the calculation method of the average particle diameter of the lipid from the scattering coefficient $\mu_s'$, a method of observing a correlation with a dynamic light scattering method (hereinafter referred to simply as a DLS method) is available. A DLS is a device for measuring an average particle diameter and a particle number distribution of particles in a suspension by dynamic light scattering.

Figure 4A:
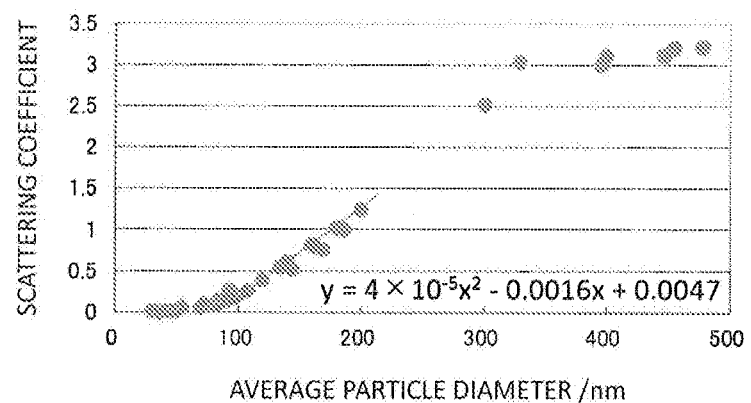
FIG. 4A is a diagram illustrating a measurement result of a variation of a scattering coefficient with an increase in an average particle diameter of a lipoprotein.

FIG. 4A shows a calibration curve for calculating the variation of the average particle diameter of the lipid in the blood from the variation of the scattering coefficient. This shows a correlation diagram between the variation of the average particle diameter and the variation of the scattering coefficient $\mu_s'$ obtained by randomly mixing latex particles of 25 nm to 500 nm so as to approximate to a distribution of the lipoprotein in the living body. Note that the concentration of the latex is about 250 mg/dL. An increase of the average particle diameter (Δparticle diameter) is obtained from a difference of the scattering coefficient values (Δ□$\mu_s'$) obtained before and after suspension of the blood using the calibration curve shown in FIG. 4A.

Figure 4B:
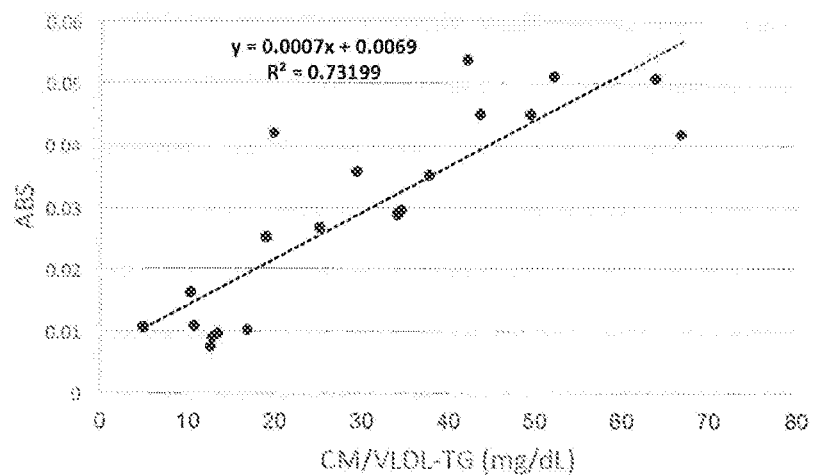
FIG. 4B is a diagram illustrating a correlation between CM/VLDL-TG and an absorbance.
Figure 4C:
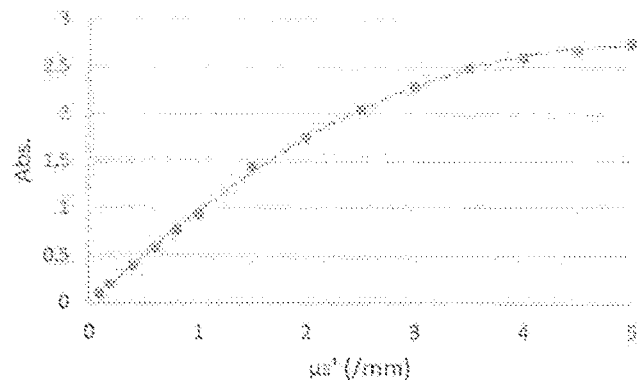
FIG. 4C is a diagram illustrating a correlation between the scattering coefficient and the absorbance.

An absorbance (ABS) of CM/VLDL-TG in the serum is measured to find a correlation as shown in FIG. 4B. Further, as shown in FIG. 4C, a correlation between the scattering coefficient $\mu_s'$ and the absorbance can be confirmed. That is, if the ABS is 0.05 in FIG. 4B, the variation of the scattering coefficient $\mu_s'$ is also 0.05/mm. Then, it can be confirmed that the variation of the average particle diameter is 75 to 100 nm from FIG. 4A.

The physical condition management can be performed only by confirming the variation of the average particle diameter of the lipoprotein. Thus, the physical condition can be easily managed without performing a conventional lipid test. The physical condition described herein comprehensively includes confirmation of an exercise effect, nutrition absorption by a meal, confirmation of a nutrition absorption control effect by medication, a supplement, and the like, a health management, and the like.

Figure 5A:
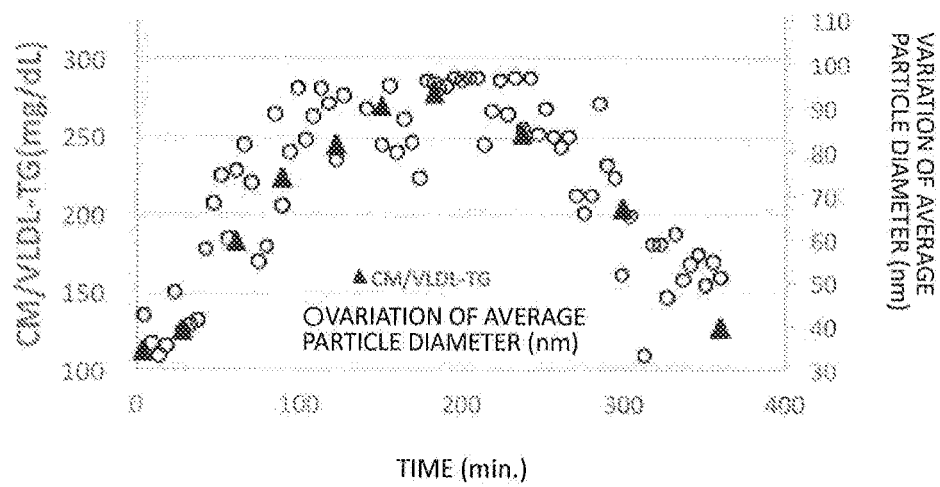
FIG. 5A is a diagram illustrating data measured in a healthy person using the physical condition management device of the present embodiment.
Figure 5B:
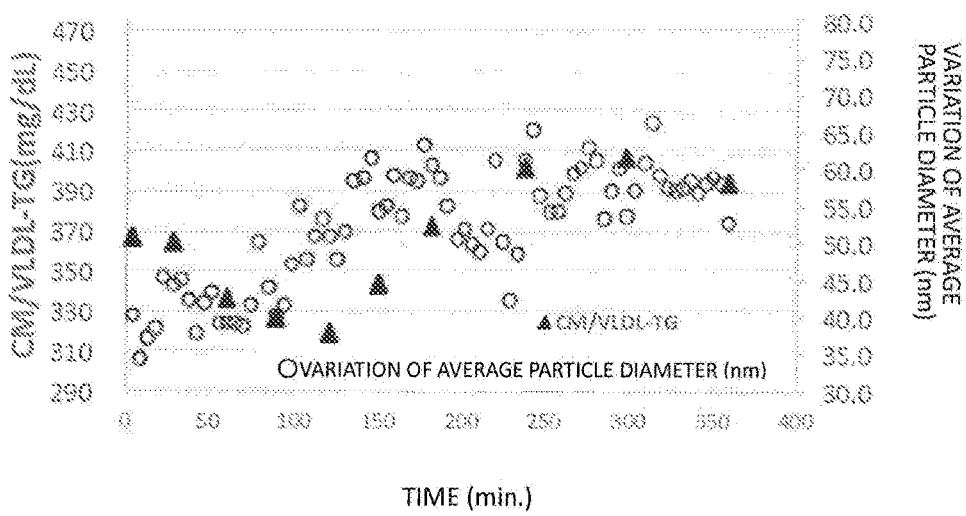
FIG. 5B is a diagram illustrating data measured in a person having a functional disorder in the liver using the physical condition management device of the present embodiment.

FIGS. 5A and B show data measured using the non-invasive physical condition management device of the present embodiment. A concentration of CM/VLDL-TG after blood collection and the fluctuating average particle diameter of the lipoprotein fluctuate synchronously. This shows that the non-invasive measurement is possible, the scattering coefficient $\mu_s'$ can be measured, and the fluctuating particle diameter of the lipoprotein particle can be derived and measured from the scattering coefficient $\mu_s'$. Further, a healthy person (FIG. 5A) and a person having a functional disorder in the liver (FIG. 5B) can be distinguished without measuring the lipid concentration.

The physical condition management measuring device 10 acquires the variation of the average particle diameter of the lipoprotein calculated by the scattering coefficient calculation unit 4 and the particle diameter calculation unit 5 and determines a lipid metabolism condition and the physical condition from a temporal change in the variation of the average particle diameter of the lipoprotein. As shown in FIG. 1, the physical condition management measuring device 10 of the present embodiment is connected to the particle diameter calculation unit 5 via a communication line or the like. The physical condition management measuring device 10 includes a calculated value acquisition unit 101 configured to acquire the variation of the average particle diameter of the lipid calculated by the particle diameter calculation unit 5 at every predetermined time and a physical condition determination unit 102 configured to determine the lipid metabolism condition and the physical condition in accordance with the temporal change in the variation of the average particle diameter acquired by the calculated value acquisition unit 101.

Note that no particular limitation is imposed on the time interval for acquiring the variation of the average particle diameter of the lipid by the calculated value acquisition unit 101. The time interval may be adjusted to an interval of several seconds to several tens of minutes or more in accordance with a test object.

Further, the acquisition of the variation of the average particle diameter of the lipid is not limited to a configuration using the communication line, and the variation of the average particle diameter of the lipid calculated by the particle diameter calculation unit 5 may be manually inputted. Further, the present embodiment is configured such that the particle diameter calculation unit 5 and the physical condition management measuring device 10 are formed as a separate member, however, the present invention is not limited to such a configuration.

The physical condition determination unit 102 determines the physical condition of an examinee from the temporal change in the variation of the average particle diameter of the lipid acquired by the calculated value acquisition unit 101. For example, time until the variation of the average particle diameter of the lipid reaches the maximum value represents digestion and absorption of the lipid by the stomach and small intestine. The health is determined in accordance with the length of such time. Further, lipolytic activity of the liver is determined by time until the variation of the average particle diameter of the lipid becomes the same value as that at fasting time. Finally, the overall health condition is determined by comprehensively examining these factors.

Figure 6:
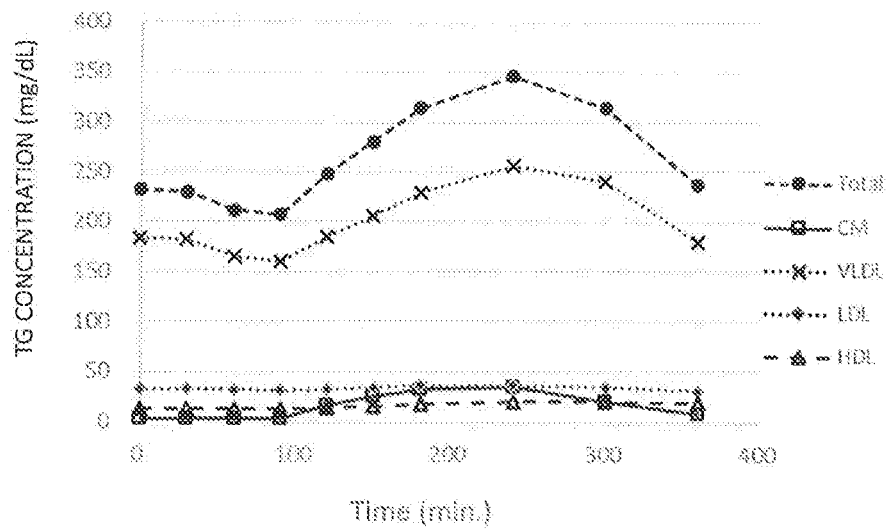
FIG. 6 is a diagram illustrating an in-day fluctuation of a lipoprotein concentration.
Figure 7A:
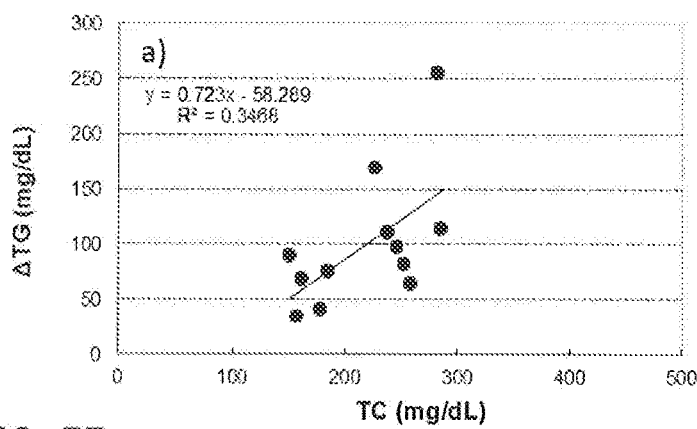
FIG. 7A is a diagram illustrating a correlation with a TG concentration in the total lipoproteins.
Figure 7B:
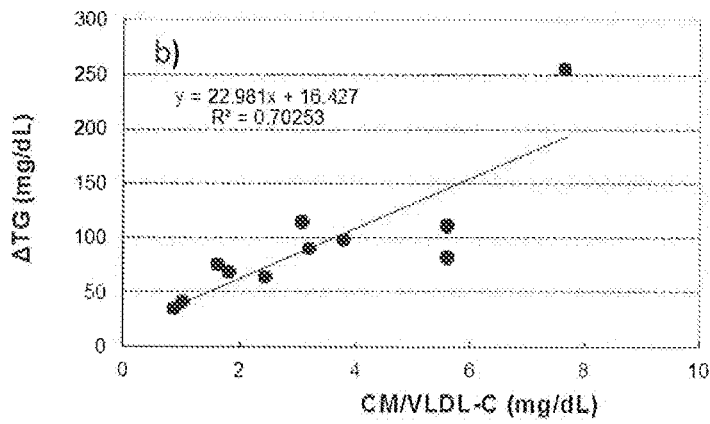
FIG. 7B is a diagram illustrating a correlation with the TG concentration in CM and VLDL.

As shown in FIG. 6, CM and VLDL have the largest in-day fluctuation of the lipoprotein concentration. As shown in FIG. 7A, there is hardly a good correlation with the TG concentration in the total lipoproteins. However, as shown in FIG. 7B, there is a good correlation with the TG concentration in CM and VLDL, and thus it can be said that the variation of the scattering coefficient $\mu_s'$ in the blood has a good correlation with the TG concentration in CM and VLDL.

Figure 8:
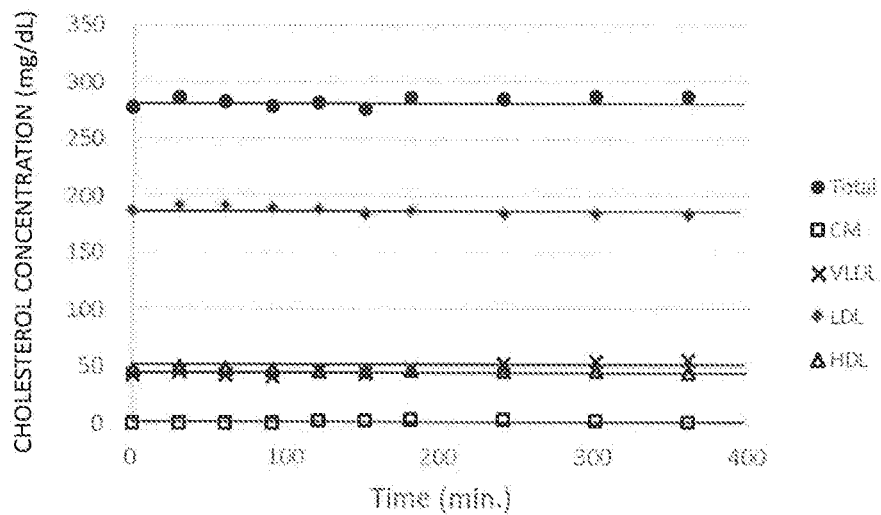
FIG. 8 is a diagram illustrating an in-day fluctuation of the total amount of cholesterol.

As shown in FIG. 8, there is little variation in an in-day fluctuation of the total amount of the cholesterols in the blood. Similarly, there is little variation in the amount of the cholesterol contained in CM and VLDL. That is, the TG concentration increases without increasing the amount of the cholesterol contained in one particle of the lipoprotein, and thus it can be assumed that the particle diameter of the lipoprotein per particle changes in accordance with an increase in the TG concentration.

Thus, it can be assumed that the TG concentration with respect to the amount of the cholesterol in each of CM and VLDL as a measurement object represents the variation of the average particle diameter of the lipoprotein. That is, the variation of the scattering coefficient $\Delta\mu_s'$ associated with the increase in the average particle diameter ($\Delta$particle diameter) of the lipoprotein satisfies the following relation.

$$\Delta\mu_s'=(CM\text{-}TG/CM\text{-}C)+(VLDL\text{-}TG/VLDL\text{-}C) \quad \text{(Equation 3)}$$

In this equation, CM-TG represents the TG concentration in the chylomicron particle, CM-C represents the cholesterol concentration in the chylomicron particle, VLDL-TG represents the TG concentration in the VLDL particle, and VLDL-C represents the cholesterol concentration in the VLDL particle.

FIG. 4A shows a result of actual measurement of the variation of the scattering coefficient $\Delta\mu_s'$ associated with the increase in the average particle diameter ($\Delta$particle diameter) of the lipoprotein. As shown in FIG. 4A, using a quadratic equation (for example, $y=4\times10^{-5}x^2-0.0016x+0.0047$) based on relatively complete data up to the average particle diameter of 200 nm, the variation of the average particle diameter ($\Delta$particle diameter) of the lipoprotein can be calculated by applying the variation of the scattering coefficient $\Delta\mu_s'$ to the quadratic equation.

Further, hyperlipidemia is categorized in type I to type V. In a case where a type-specific change in the lipid particle is found to determine some type of hyperlipidemia, the above-described Equation 3 can be modified as the following Equation 4 by including a type-specific coefficient to improve accuracy of the measurement.

$$\Delta\mu_s'=A\cdot(CM\text{-}TG/CM\text{-}C)+B\cdot(VLDL\text{-}TG/VLDL\text{-}C) \quad \text{(Equation 4)}$$

In this equation, A represents a scattering intensity correction coefficient for CM, B represents a scattering intensity correction coefficient for VLDL, CM-TG represents the TG concentration in the chylomicron particle, CM-C represents the cholesterol concentration in the chylomicron particle, VLDL-TG represents the TG concentration in the VLDL particle, and VLDL-C represents the cholesterol concentration in the VLDL particle.

The physical condition management device of the present embodiment may include a current application unit configured to apply a pulse current to the inside of the living body. The lipid particle is charged and a zeta potential is different depending on the type of the lipoprotein. By utilizing such feature, CM or VLDL is caused to vibrate by applying the pulse current to the inside of the body from the outside of the body using the current application unit. This causes a variation in the scattering coefficient, thereby making it possible to measure the distribution of the lipoprotein more accurately.

The physical condition determination unit 102 of the present embodiment determines the metabolism condition of the living body from the temporal change in the variation of the average particle diameter of the lipid and then determines the physical condition. Since the large lipoprotein has a relatively high metabolism rate, it can be used to determine the condition of an organ related to the metabolism.

The physical condition determination unit 102 of the present embodiment determines a risk of arteriosclerosis from residence time of the variation of the average particle diameter of the lipid in the blood. This can be used as the indication that the lipid as a causing factor for arteriosclerosis tends to accumulate in the blood vessel when retained in the blood for a long time.

The physical condition determination unit 102 of the present embodiment determines timing of insulin secretion from the temporal change in the variation of the average particle diameter of the lipid in the blood. When the variation of the average particle diameter of the lipid in the blood and a blood sugar level are measured at the same time, an increase in the lipid concentration and an increase in the scattering caused by the lipoprotein are temporarily suppressed at the time when the blood sugar reaches the peak. This coincides with the timing of insulin secretion and captures a phenomenon in which the insulin secretion is given priority over the lipid in the body. It can be assumed that this is caused by increasing activity of the insulin, which in turn enhances LPL activity in the capillary and activates a metabolism rate (reduces a particle size) of CM.

The physical condition determination unit 102 of the present embodiment determines a delay in insulin secretion from the timing of insulin secretion to detect insulin resistance.

The physical condition determination unit 102 of the present embodiment determines diabetes from the insulin resistance. As described above, an abnormality in a blood sugar control can be determined from the insulin resistance, and thus the device can be used to examine and control diabetes.

The physical condition determination unit 102 of the present embodiment obtains a lipid absorption amount (an increasing amount of a triglyceride concentration) by a meal from the increase of the variation of the average particle diameter of the lipid in the blood. Using a fat loading diet or the like allows more accurate examination of the absorption amount, thereby making it possible to grasp physical characteristics or the like.

The physical condition determination unit 102 of the present embodiment stores previously prepared statistical data of the variation of the average particle diameter of the lipid, determines the existence of abnormality by comparing the statistical data and detected variation of the average particle diameter of the lipid, determines the physical condition on the basis of the determination result, and performs a nutritional guidance and a medication management. The lipid absorption amount differs from person to person, however, a dosage of a lipid absorption inhibitor or the like sufficiently exhibiting a medicinal efficacy can be individually managed. Further, the device can also be used for a nutrition absorption management exercising ingenuity in a combination of food or the like.

Figure 9:
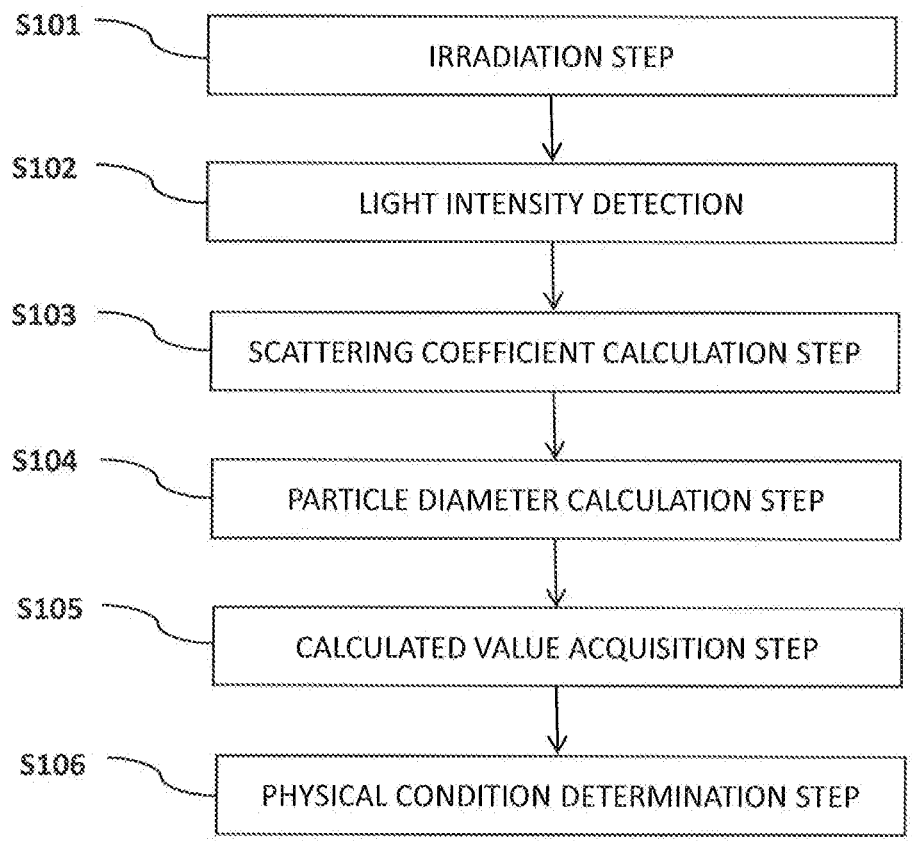
FIG. 9 is a flowchart of an operation method of the physical condition management device of the present embodiment.

Next, the operation method of the physical condition management device of the present embodiment will be described. FIG. 9 shows a flowchart of the operation method of the physical condition management device of the present embodiment.

In an irradiation step (S101), the continuous light is radiated from the irradiation position 21 using the irradiation unit 2.

In a light intensity detection step (S102), the first light intensity detection unit 31 is used to detect the light intensity at the first detection position 331 and the second light intensity detection unit 32 is used to detect the light intensity at the second detection position 332. The light intensities detected at the first detection position 331 and the second detection position 332 are sent to a scattering coefficient calculation step.

In a scattering coefficient calculation step (S103), a light intensity difference or a light intensity ratio between a first light intensity at the first detection position 331 and a second light intensity at the second detection position 332 is calculated and then the scattering coefficient $\mu_s'$ is calculated on the basis of the light intensity difference or the light intensity ratio. The scattering coefficient $\mu_s'$ thus calculated is sent to a particle diameter calculation step.

In a particle diameter calculation step (S104), the variation of the average particle diameter of the lipoprotein in the blood is calculated from the variation of the scattering coefficient $\mu_s'$.

In a calculated value acquisition step (S105), the variation of the average particle diameter of the lipoprotein thus calculated is acquired via the communication line and sent to a physical condition determination step.

In a physical condition determination step (S106), the physical condition is determined on the basis of the temporal change in the variation of the average particle diameter of the lipoprotein. For example, the maximum value of the variation of the average particle diameter, the time until the variation of the average particle diameter reaches the maximum value, the time until the variation of the average particle diameter comes back to the value at the fasting time through the maximum value, the absorption amount of the lipid, and the like are obtained.

Then, the existence of abnormality is determined from each value by comparing previously prepared statistical data of the variation of the average particle diameter of the lipid and measured variation of the average particle diameter of the lipid. If the value is a normal value, the physical condition is determined to be normal, and if the value is deviated from a normal value, the physical condition is determined to be not normal.

For example, if the maximum value of the variation of the average particle diameter of the lipid is within a normal value, a basal metabolism of the lipid is determined to be normal, and if it is out of the normal value, the basal metabolism of the lipid is determined to be not normal. Similarly, if the time until the variation of the average particle diameter of the lipid reaches the maximum value is within a normal value, a function of digestion and absorption of the lipid by the stomach and small intestine is determined to be normal, and if it is out of the normal value, the function of digestion and absorption by the stomach and small intestine is determined to have some abnormality. Further, if the time until the variation of the average particle diameter of the lipid becomes the same value as that at the fasting time is within a normal value, the lipolytic activity of the liver is determined to be normal, and if it is out of the normal value, the lipolytic activity of the liver is determined to be not normal.

In the physical condition determination step of the present embodiment, the metabolism condition of the living body is measured from the temporal change in the variation of the average particle diameter of the lipoprotein in the blood. The large lipoprotein has a relatively high metabolism rate, and thus it can be used to determine the condition of the organ related to the metabolism.

In the physical condition determination step of the present embodiment, a risk of arteriosclerosis is determined from the residence time of the variation of the average particle diameter of the lipoprotein in the blood. This can be used as the indication that the lipid as a causing factor for arteriosclerosis tends to accumulate in the blood vessel when retained in the blood for a long time.

In the physical condition determination step of the present embodiment, the timing of insulin secretion is determined from the temporal change in the variation of the average particle diameter of the lipoprotein in the blood. When the variation of the average particle diameter of the lipoprotein in the blood and the blood sugar level are measured at the same time, the lipid increase is temporarily suppressed at the time when the blood sugar reaches the peak. This coincides with the timing of insulin secretion and captures the phenomenon in which the insulin secretion is given priority over the lipid in the body.

In the physical condition determination step of the present embodiment, the insulin resistance is detected from the timing of insulin secretion. As described above, the insulin resistance such as a delay in insulin secretion can be detected by successfully measuring the insulin secretion time.

In the physical condition determination step of the present embodiment, diabetes is examined from the insulin resistance. As described above, the abnormality in the blood sugar control can be indicated by detecting the insulin resistance, and thus the method can be used to examine and control diabetes.

In the physical condition determination step of the present embodiment, the lipid absorption amount by a meal is obtained from the increase of the variation of the average particle diameter of the lipoprotein in the blood. Using the fat loading diet or the like allows more accurate examination of the absorption amount, thereby making it possible to grasp physical characteristics or the like.

In the physical condition determination step of the present embodiment, an individual difference in the nutrition absorption is examined to perform the nutritional guidance and the medication management from the increase of the variation of the average particle diameter of the lipoprotein in the blood by storing the previously prepared statistical data of the variation of the average particle diameter of the lipoprotein and comparing the statistical data and detected average particle diameter of the lipoprotein. The nutrition absorption differs from person to person, however, a dosage of a lipid absorption inhibitor or the like sufficiently exhibiting a medicinal efficacy can be individually managed. Further, the method can also be used for the nutrition absorption management exercising ingenuity in a combination of food or the like.

In the physical condition determination step of the present embodiment, a current application step in which a pulse current is applied to the inside of the body from the outside of the body is included to cause a change in the scattering coefficient by vibrating CM or VLDL, thereby making it possible to measure the distribution of the lipoprotein more accurately.

As described above, according to the physical condition management device and the operation method thereof of the present embodiment, the individual difference in a nutrition absorption rate, a fatigue degree check, the diabetes control, the metabolic syndrome control, the liver function test, the risk management of arteriosclerosis can be measured by measuring the variation of the average particle diameter of the lipoprotein such as CM and VLDL. This makes it possible to perform the early detection of the metabolic disease, the nutritional guidance, and diagnosis of the physical condition management.

Next, the physical condition management device of another embodiment of the present invention will be described. Note that a configuration of the physical condition management device of another embodiment of the present invention includes a part which is common to the configuration of the physical condition management device of the above-described embodiment, and thus the description will primarily focus on a part different from the above-described embodiment.

The above-described embodiment shows the configuration example in which the irradiation unit 2, the light intensity detection unit 3, the scattering coefficient calculation unit 4, the particle diameter calculation unit 5, and the physical condition management measuring device 10 are formed as a single member and the configuration example in which the irradiation unit 2, the light intensity detection unit 3, the scattering coefficient calculation unit 4, the particle diameter calculation unit 5, and the physical condition management measuring unit 10 are formed as separate members. However, the present invention is not limited to these examples, and may provide a system configured from a user device that includes the irradiation unit 2 configured to radiate the light and the light intensity detection unit 3 and a physical condition management device that includes the scattering coefficient calculation unit 4, the particle diameter calculation unit 5, the calculated value acquisition unit 101, and the physical condition determination unit 102.

Figure 19:
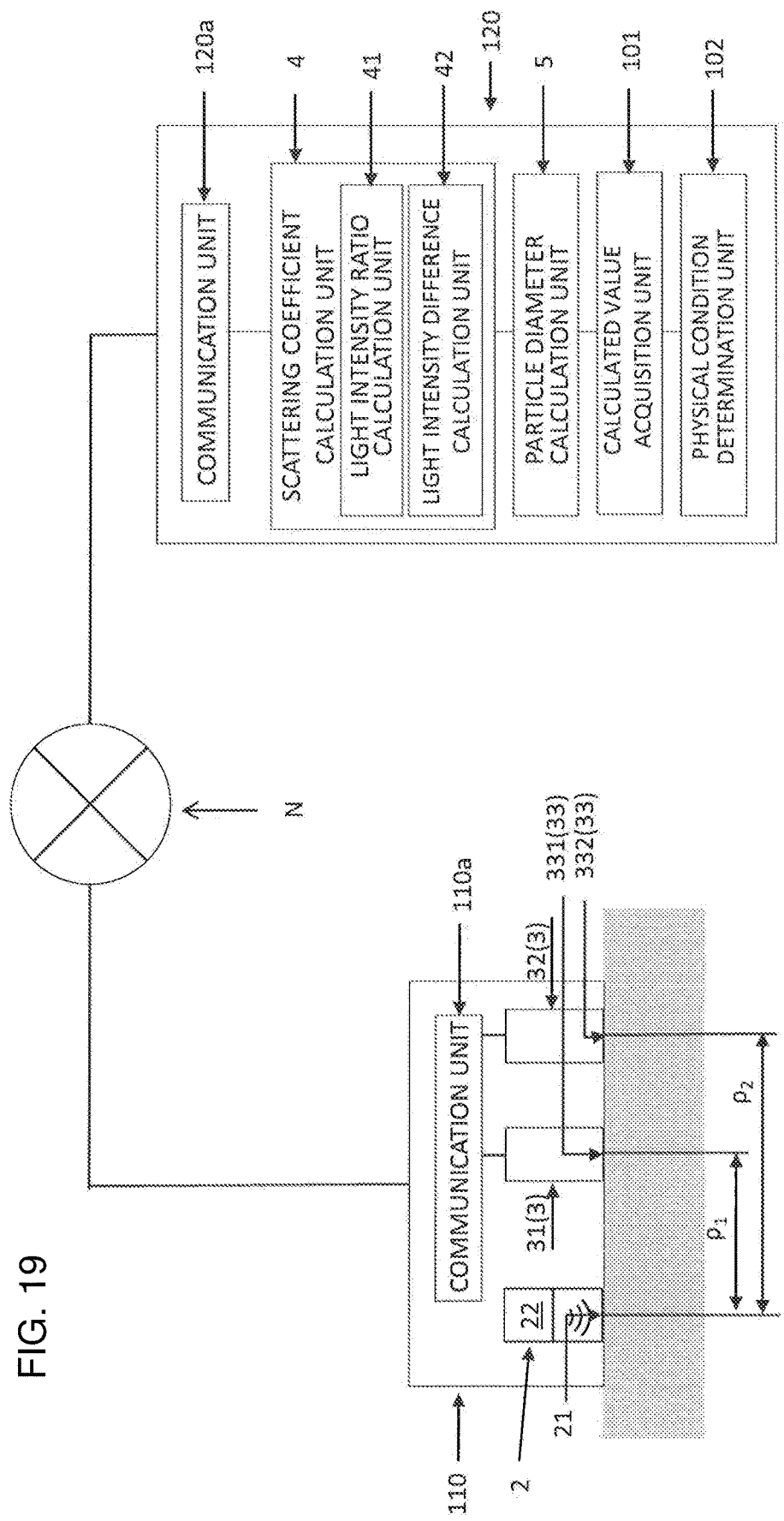
FIG. 19 is a block diagram illustrating a configuration of a physical condition management system of the present embodiment.

FIG. 19 is a block diagram illustrating the configuration of the physical condition management system of the present embodiment. A user device 110 and a physical condition management device 120 used in the physical condition management system of the present embodiment each include a CPU (arithmetic unit) and a memory device (storage unit such as a RAM and a ROM) and function as the device shown in the block diagram in FIG. 19 by executing a program stored in the memory device.

The physical condition management system of the present embodiment is configured from the user device 110 configured to measure the light intensity and the physical condition management device 120 configured to determine the physical condition from the light intensity. The user device 110 and the physical condition management device 120 are connected to a network via a wireless or wired communication network N.

The physical condition management device 120 is a device configured to perform a predetermined process on the basis of the light intensity sent from the user device 110 to determine the physical condition. Specifically, a personal computer or a server apparatus, depending on the number of the devices and an amount of data to be transmitted and received, may be appropriately used.

The user device 110 is a device that is carried by a user. The user device 110 is used as a single device or mounted on a cellular phone, a wristwatch, or the like.

The user device 110 includes the irradiation unit 2 configured to radiate the light, the light intensity detection unit 3, and a communication unit 110a. The communication unit 110a sends the light intensity detected by the light intensity detection unit 3. The functions and operations of the irradiation unit 2 and the light intensity detection unit 3 have been described above.

The physical condition management device 120 includes a communication unit 120a, the scattering coefficient calculation unit 4, the particle diameter calculation unit 5, the calculated value acquisition unit 101, and the physical condition determination unit 102. The communication unit 120a receives the light intensity sent from the communication unit 110a via the wired or wireless network N and send it to the scattering coefficient calculation unit 4. The functions and operations of the scattering coefficient calculation unit 4, the particle diameter calculation unit 5, the calculated value acquisition unit 101, and the physical condition determination unit 102 have been described above.

Note that, in the present embodiment, the light intensity is sent from the user device 110 to the physical condition management device 120 via the network N. However, the present invention is not limited thereto, and the user device 110 may be directly connected to the physical condition management device 120 without using the network N and then the light intensity may be sent by a means such as a wired communication and a wireless communication.

The physical condition management device of the present embodiment is communicatively connected to the user device that includes: the irradiation unit configured to radiate the light at a predetermined intensity of light toward the inside of the living body from the outside of the living body; the light intensity detection unit configured to detect the intensity of the light emitted from the living body for measuring the attenuation of the light intensity of the radiated light corresponding to the radiation-detection distance, the light intensity detection unit being arranged at a predetermined interval from or continuously with the light irradiation position of the irradiation unit; and the communication unit configured to send the light intensity detected by the light intensity detection unit, the physical condition management device including: the scattering coefficient calculation unit configured to calculate the scattering coefficient of the light inside the living body on the basis of the light intensity sent from the user device; the particle diameter calculation unit configured to calculate the variation of the average particle diameter of the lipid in the blood on the basis of the variation of the scattering coefficient; and the physical condition determination unit configured to determine the physical condition from the temporal change in the variation of the average particle diameter.

Further, in the physical condition management device of the present embodiment, the irradiation position is arranged at the predetermined radiation-detection distance from the detection position for detecting the light intensity, and thus the light intensity detection unit detects the light intensity of the back scattered light scattered by the lipid in the blood.

Further, in the physical condition management device of the present embodiment, the irradiation unit is the light source configured to emit the continuous light, the light being radiated from the light source. The plurality of light intensity detection units each arranged at a different distance from the irradiation position serving as a substantial center detect the light intensities at each detection position, and the scattering coefficient calculation unit calculates the scattering coefficient of the light inside the living body on the basis of the ratio of the light intensities or the difference of the light intensities detected by the respective light intensity detection units.

Further, the physical condition determination unit of the physical condition management device of the present embodiment determines the risk of arteriosclerosis, the metabolic function of the liver, or the fatigue degree from the temporal change in the variation of the average particle diameter.

Further, the physical condition determination unit of the physical condition management device of the present embodiment determines the timing of insulin secretion from the temporal change in the variation of the average particle diameter and then measures the insulin resistance from the timing of insulin secretion.

Further, the physical condition management device of the present embodiment further includes the current application unit configured to apply a pulse current to the inside of the living body.

Further, in the physical condition management device of the present embodiment, the lipid is chylomicron or VLDL.

EXAMPLES

Examples of the present invention will be described below. However, the present invention is not limited to the following examples.

(1) Measurement of Average Particle Diameter of Lipoprotein

CM and VLDL are lipoproteins of which levels increase after a meal. In-day fluctuations of other lipoproteins are negligible.

As evident from FIG. 6, when the lipid is actually measured after a meal, the measurement value of the triglyceride (TG) fluctuates. However, as shown in FIG. 8, the cholesterol stays constant. That is, it can be confirmed that the in-day fluctuation of the TG concentration is caused by the variation of the TG concentration in CM and VLDL forming large particles.

Figure 10:
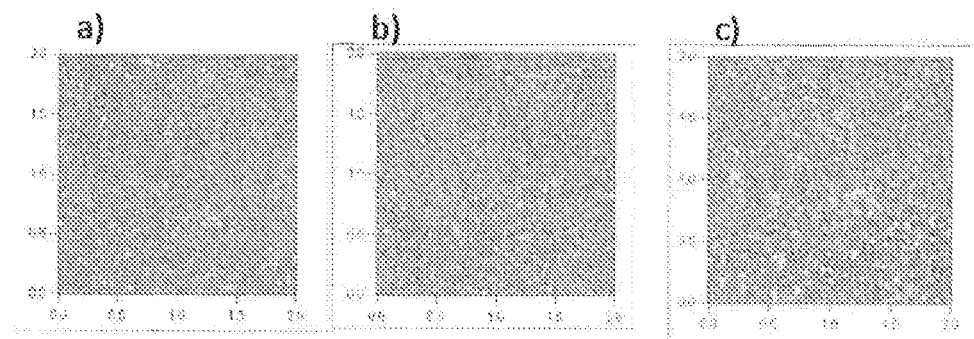
FIG. 10 is images of the serum captured by an atomic force microscope.

FIG. 10 shows images of the serum captured by an atomic force microscope before fat loading ((a) in FIG. 10), 60 minutes after fat loading ((b) in FIG. 10), and 180 minutes after fat loading ((c) in FIG. 10). White spots represent the lipoproteins. As shown in FIG. 10, it could be confirmed that the size of the particle became larger 180 minutes after the meal ((c) in FIG. 10).

Figure 11:
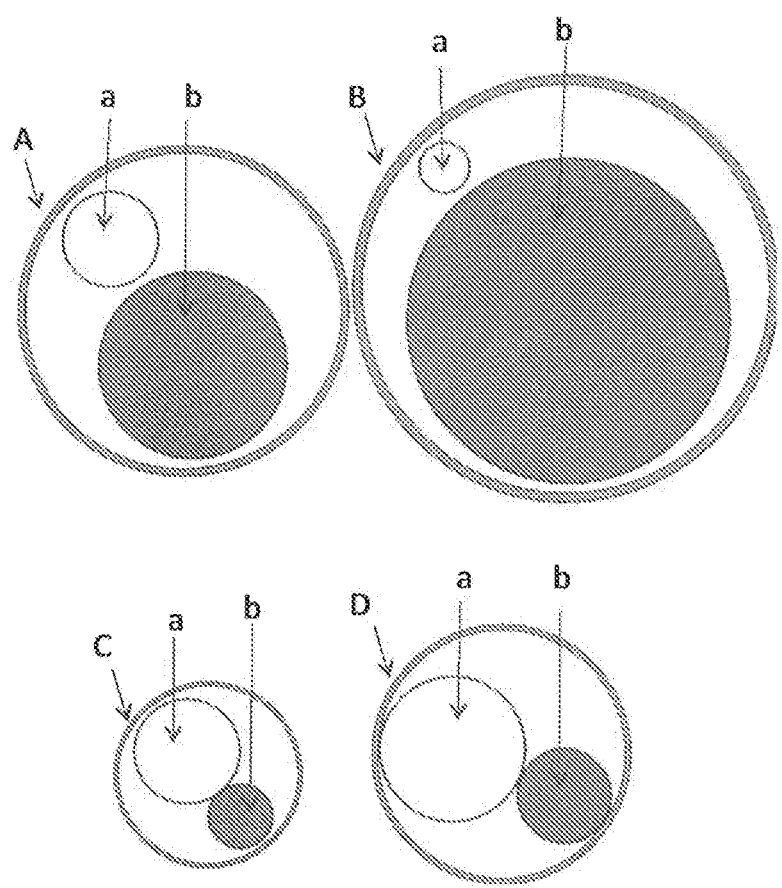
FIG. 11 is a diagram illustrating a concept of the lipoprotein.
Figure 12:
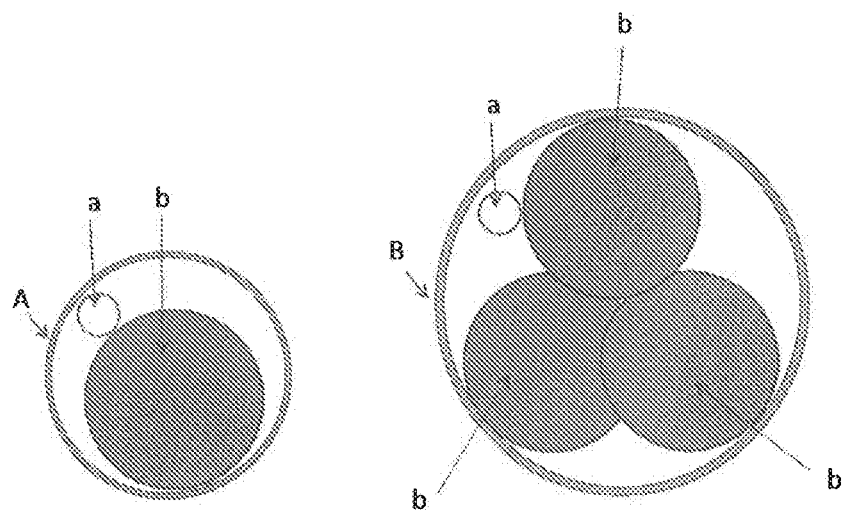
FIG. 12 is a diagram illustrating the concept of the lipoprotein.

FIGS. 11 and 12 each are a diagram illustrating a concept of the lipoprotein. In FIG. 11, "A" represents VLDL, "B" represents chylomicron, "C" represents HDL, and "D" represents LDL. Further, "a" represents the cholesterol and "b" represents TG. The concentration of the triglyceride (TG) increases while the cholesterol concentration remains constant, and thus it can be assumed that the scattering caused by the lipid increased as the average particle diameters of the lipoproteins represented by "A", "B", "C", and "D" in FIG. 11 increased. It can be assumed that the particle diameters of "A" and "B" become larger particularly after the meal and "A" and "B" having large particle diameters have a great influence on the scattering intensity.

In FIG. 12, "A" represents chylomicron and "B" represents chylomicron after the meal. Further, "a" represents the cholesterol and "b" represents TG. As shown in FIG. 12, there is a limitation to the increase in the average particle diameter of the lipoprotein per particle and the lipoprotein does not expand infinitely. That is, the same chylomicron (CM) ranges from relatively small size with an empty storage room ("A" in FIG. 12) to enlarged size with a packed storage room ("B" in FIG. 12).

The increase in the scattering after the meal measured in this example reflects the increase in the average particle diameter of the lipoprotein. Thus, the scattering coefficient has a good correlation with (CM-TG)/(CM-TC)+(VLDL-TG)/(VLDL-TC).

(Example 1) Individual Difference of Fat Absorption Rate

A drug absorption rate check, a fat loading test, and the like are conventionally performed with an estimation so as to obtain a constant blood concentration by correcting a dosage using a surface area of the body or the like.

Figure 13:
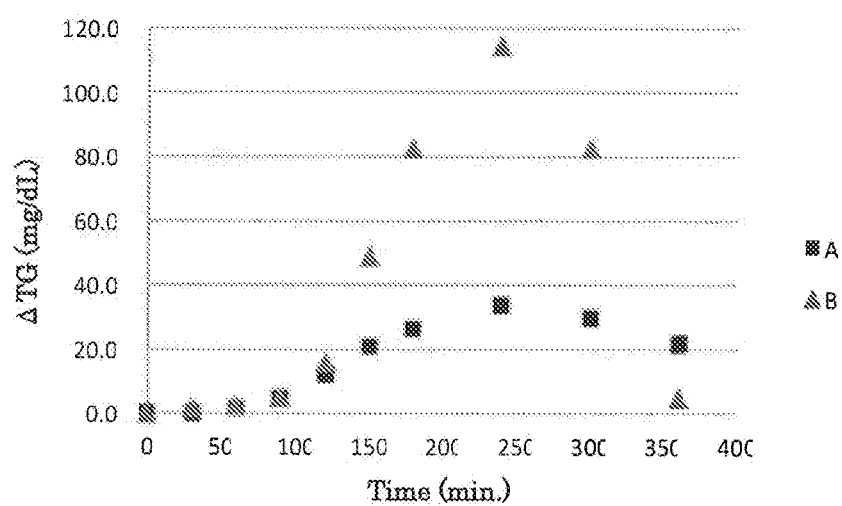
FIG. 13 is a diagram illustrating a test result in which a male and a female having different physical sizes are asked to ingest the same amount of OFTT cream.
Figure 14:
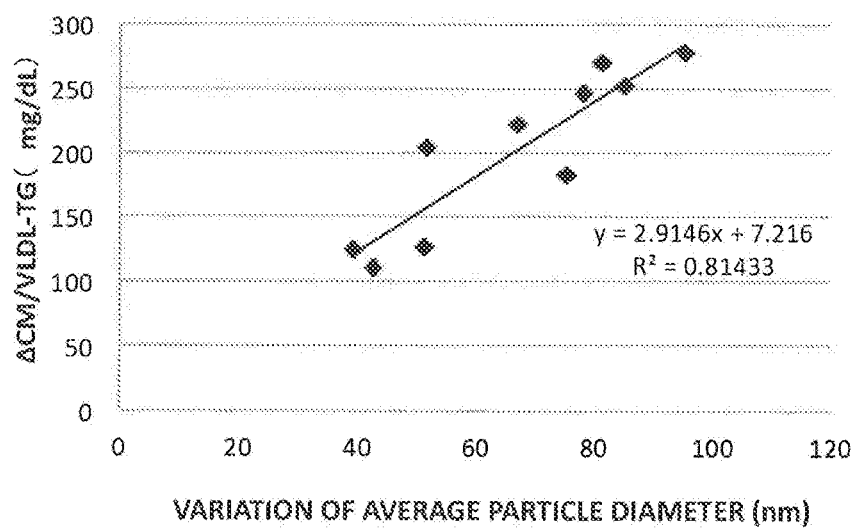
FIG. 14 is a diagram illustrating a correlation between an increasing amount of a triglyceride and a variation of a particle diameter.
Figure 15:
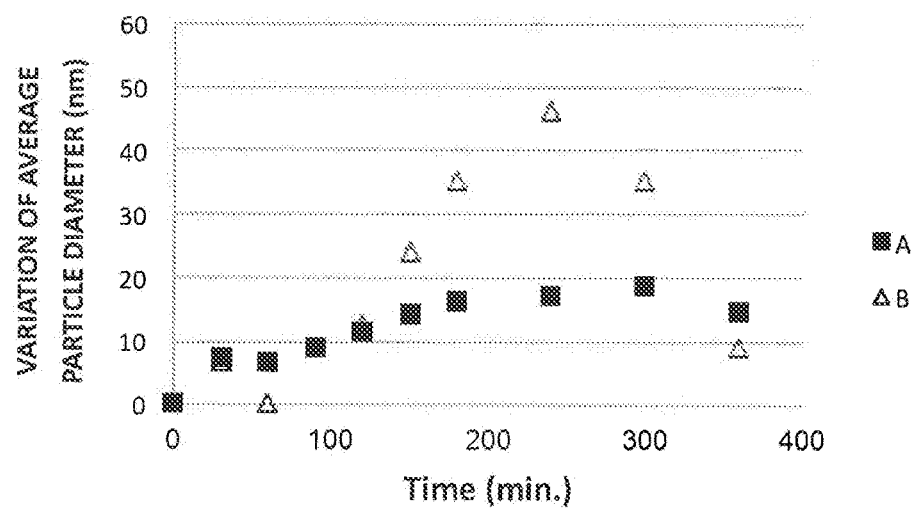
FIG. 15 is a diagram illustrating a graph in FIG. 13 in which the item in a vertical axis is converted to a variation of an average particle diameter.

However, as shown in FIG. 13, when a male ("B" in FIG. 13) who weighs 90 kg or more and a female ("A" in FIG. 13) who weighs 50 kg or less were both asked to ingest 160 g of OFTT cream, the triglyceride (TG) concentration in the male ("B" in FIG. 13) increased by 100 mg/dL or more, while the triglyceride (TG) concentration in the female ("A" in FIG. 13) increased by only about 50 mg/dL. That is, this showed that there was clearly an individual difference even if the same amount of nutrient having the same ingredient was ingested. Further, the increasing amount of the triglyceride can be converted to the variation of the particle diameter as shown in FIG. 14. Accordingly, the graph in FIG. 13 can be converted into the graph in FIG. 15, thereby allowing the physical condition management using the variation of the average particle diameter. The variation of the average particle diameter can also be converted into the triglyceride concentration.

Thus, when the physical condition management device and the method thereof of this example are used, physical characteristics such as a tendency of absorbing the fat are visualized as shown in FIG. 13, and thus the device and method can be used to perform a personalized nutrition management guidance or the like.

Further, an effect of the lipid absorption inhibitor or the like can be measured by using the physical condition management device and the method thereof of this example.

(Example 2) Fatigue Degree Check

Figure 16:
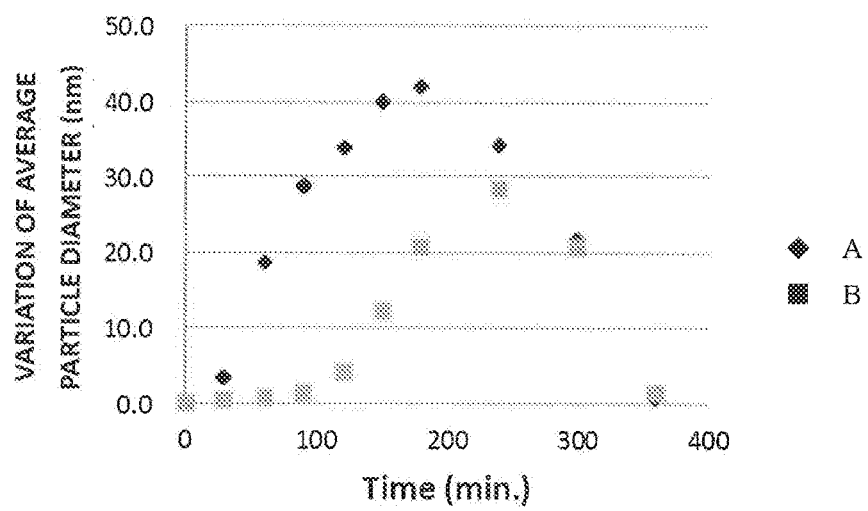
FIG. 16 is a diagram illustrating a comparison of absorption time of a fat.

FIG. 16 is a diagram illustrating a comparison of fat absorption time in a male examinee in his 40s between in a fatigue condition after working all night ("B" in FIG. 16) and a normal working condition without having overtime ("A" in FIG. 16).

When the comparison was made by asking the examinee to ingest 160 g of OFTT cream, there was a difference in the temporal change in the variation of the average particle diameter as shown in FIG. 16. Thus, when the physical condition management device and the method thereof of this example are used, some abnormal physical condition can be visualized from the temporal change in the variation of the average particle diameter and notified to a third party.

Further, when an absorption pattern is daily recorded using the physical condition management device and the method thereof of this example, the record can be used for the physical condition management and health consultation.

(Example 3) Diabetes Control/Metabolic Syndrome Control

In this example, the average particle diameter of the lipid was continuously measured at the same time when the blood sugar having a high in-day fluctuation was measured. Daily changes were examined after a daily meal was ingested.

Figure 17:
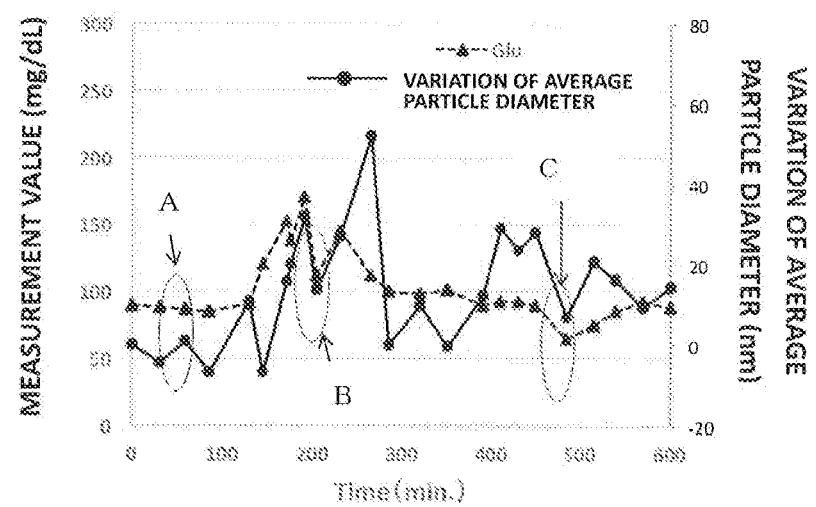
FIG. 17 is a diagram illustrating a result in which the average particle diameter of a lipid, and a blood sugar are measured at the same time.

As a result, as shown in FIG. 17, it was found that the variation of the average particle diameter of CM and VLDL in the blood fluctuated closely with the blood sugar level. Note that, in FIG. 17, "A" indicates a meal, "B" indicates insulin secretion, and "C" indicates hunger feeling. Further, discharge of the lipid into the blood is suppressed at the time when insulin is secreted ("B" in FIG. 17), and thus the insulin resistance as a cause of the metabolic syndrome can be measured by detecting the timing of insulin secretion.

Further, it was found that the blood sugar decreased along with a decrease in the variation of the average particle diameter of CM and VLDL at the time when an examinee felt hunger ("C" in FIG. 17). Thus, it was found that the early detection and control of diabetes could also be performed by measuring the temporal change in the variation of the average particle diameter of CM and VLDL using the physical condition management device and the method thereof of this example.

(Example 4) Test of Liver Function

Since the lipid is metabolized in the liver, it was examined whether an evaluation indicator such as lipid metabolic time can be used for evaluating the liver function.

Figure 18:
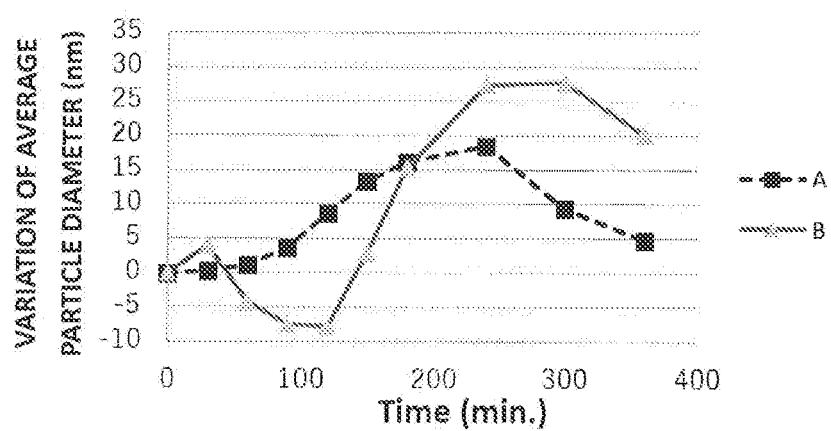
FIG. 18 is a diagram illustrating a result in which a metabolic function of the liver is evaluated.

As shown in FIG. 18, the temporal change in the variation of the average particle diameter of the lipid in an examinee diagnosed as fatty liver by a physician ("A" in FIG. 18) became slower than that in a healthy person ("B" in FIG. 18), confirming that the metabolic function of the liver was evaluated.

The delay in the lipid metabolism was also observed in an examinee who regularly drank alcohol, although the examinee had test result of a physical examination as GOT=26 U/L and GPT=30 U/L falling within a reference value. Half a year later, however, the physical examination detected an abnormality in the liver function test values, GOT=38 U/L and GPT=68 U/L, and the examinee was diagnosed as a slight case of fatty liver by an echo examination.

This result showed that the physical condition management device and the method thereof of this example could provide a liver function test superior to the conventional blood test.

(Example 5) Risk Management of Arteriosclerosis

The physical condition management device and the method thereof of this example can be also used for predicting the onset of arteriosclerosis in the future by integrating the variation of the average particle diameter of CM and VLDL in the blood and the residence time of CM and VLDL in the blood in every month.

REFERENCE SIGNS LIST 1 physical condition management device
2 irradiation unit
3 light intensity detection unit
4 scattering coefficient calculation unit
5 particle diameter calculation unit
10 physical condition management measuring device
101 calculated value acquisition unit
102 physical condition determination unit
21 irradiation position
22 light source
31 first light intensity detection unit
32 second light intensity detection unit
33 detection position 331 first detection position
332 second detection position
42 light intensity ratio calculation unit
43 light intensity difference calculation unit

The invention claimed is:

1. A physical condition management device comprising:
an irradiation unit configured to radiate light at a predetermined light intensity toward an inside of a living body from an outside of the living body;
a light intensity detection unit configured to detect a light intensity emitted from the living body for measuring an attenuation of the light intensity of the radiated light corresponding to a radiation-detection distance, the light intensity detection unit being arranged at a predetermined interval from or continuously with a light irradiation position of the irradiation unit;
a scattering coefficient calculation unit configured to calculate a scattering coefficient of light inside the living body on a basis of the light intensity detected by the light intensity detection unit;
a particle diameter calculation unit configured to calculate a variation of an average particle diameter of a lipid in blood on a basis of a variation of the scattering coefficient; and
a physical condition determination unit configured to determine a physical condition from a temporal change in the variation of the average particle diameter.

2. The physical condition management device according to claim 1, wherein the irradiation position is arranged at a predetermined radiation-detection distance from a detection position for detecting the light intensity, and the light intensity detection unit detects a light intensity of back scattered light scattered by the lipid in the blood.

3. The physical condition management device according to claim 1, wherein:
the irradiation unit is a light source configured to emit continuous light, the light being radiated from the light source,
each of a plurality of light intensity detection units is arranged at a different distance from the irradiation position serving as a substantial center detect light intensities at respective detection positions; and
the scattering coefficient calculation unit calculates the scattering coefficient of the light inside the living body on a basis of a ratio of the respective light intensities or a difference of the respective light intensities detected by the respective light intensity detection units.

4. The physical condition management device according to claim 1, wherein the physical condition determination unit determines a risk of arteriosclerosis, a metabolic function of a liver, or a fatigue degree from the temporal change in the variation of the average particle diameter.

5. The physical condition management device according to claim 1, wherein the physical condition determination unit determines a timing of insulin secretion from the temporal change in the variation of the average particle diameter and measures insulin resistance from the timing of insulin secretion.

6. The physical condition management device according to claim 1, further comprising a current application unit configured to apply a pulse current to the inside of the living body.

7. The physical condition management device according to claim 1, wherein the lipid is chylomicron or VLDL.

8. An operation method of a physical condition management device, the operation method comprising:
an irradiation step of radiating light at a predetermined light intensity toward an inside of a living body from an outside of the living body;
a light intensity detection step of detecting a light intensity emitted from the living body for measuring an attenuation of the light intensity of the radiated light corresponding to a radiation-detection distance, at a position of a predetermined interval from or continuously with a light irradiation position in the irradiation step;
a scattering coefficient calculation step of calculating a scattering coefficient of light inside the living body on a basis of the light intensity detected in the light intensity detection step;
a particle diameter calculation step of calculating a variation of an average particle diameter of a lipid in blood on a basis of a variation of the scattering coefficient; and
a physical condition determination step of determining a physical condition from a temporal change in the variation of the average particle diameter.

9. The operation method of a physical condition management device according to claim 8, wherein the irradiation position is arranged at a predetermined radiation-detection distance from a detection position for detecting the light intensity, and in the light intensity detection step, a light intensity of back scattered light scattered by the lipid in the blood is detected.

10. The operation method of a physical condition management device according to claim 8, wherein:
in the irradiation step, continuous light is radiated,
light intensities at respective detection positions arranged at a different distance from the irradiation position serving as a substantial center are detected; and
in the scattering coefficient calculation step, the scattering coefficient of the light inside the living body is calculated on a basis of a ratio of the respective light intensities or a difference of the respective light intensities.

11. The operation method of a physical condition management device according to claim 8, wherein in the physical condition determination step, a risk of arteriosclerosis, a metabolic function of a liver, or a fatigue degree is determined from the temporal change in the variation of the average particle diameter.

12. The operation method of a physical condition management device according to claim 8, wherein in the physical condition determination step, a timing of insulin secretion is determined from the temporal change in the variation of the average particle diameter and insulin resistance is measured from the timing of insulin secretion.

13. The operation method of a physical condition management device according to claim 8, wherein the lipid is chylomicron or VLDL.

14. A physical condition management device configured to be communicatively connected to a user device that includes an irradiation unit configured to radiate light at a predetermined light intensity toward an inside of a living body from an outside of the living body, a light intensity detection unit configured to detect a light intensity emitted from the living body for measuring an attenuation of the light intensity of the radiated light corresponding to a radiation-detection distance, the light intensity detection unit being arranged at a predetermined interval from or continuously with a light irradiation position of the irradiation unit, and a communication unit configured to send the light intensity detected by the light intensity detection unit, the physical condition management device comprising:
a scattering coefficient calculation unit configured to calculate a scattering coefficient of light inside the living body on a basis of the light intensity sent from the user device;
a particle diameter calculation unit configured to calculate a variation of an average particle diameter of a lipid in blood on a basis of a variation of the scattering coefficient; and
a physical condition determination unit configured to determine a physical condition from a temporal change in the variation of the average particle diameter.

15. The physical condition management device according to claim 14, wherein the irradiation position is arranged at a predetermined radiation-detection distance from a detection position for detecting the light intensity, and the light intensity detection unit detects a light intensity of back scattered light scattered by the lipid in the blood.

16. The physical condition management device according to claim 14, wherein:
the irradiation unit is a light source configured to emit continuous light, the light being radiated from the light source,
each of a plurality of light intensity detection units is arranged at a different distance from the irradiation position serving as a substantial center detect light intensities at respective detection positions; and
the scattering coefficient calculation unit calculates the scattering coefficient of the light inside the living body on a basis of a ratio of the respective light intensities or a difference of the respective light intensities detected by the respective light intensity detection units.

17. The physical condition management device according to claim 14, wherein the physical condition determination unit determines a risk of arteriosclerosis, a metabolic function of a liver, or a fatigue degree from the temporal change in the variation of the average particle diameter.

18. The physical condition management device according to claim 14, wherein the physical condition determination unit determines a timing of insulin secretion from the temporal change in the variation of the average particle diameter and measures insulin resistance from the timing of insulin secretion.

19. The physical condition management device according to claim 14, further comprising a current application unit configured to apply a pulse current to the inside of the living body.

20. The physical condition management device according to claim 14, wherein the lipid is chylomicron or VLDL.

* * * * *